United States Patent
Baisakh et al.

(10) Patent No.: US 10,465,202 B2
(45) Date of Patent: Nov. 5, 2019

(54) ABIOTIC STRESS RESISTANCE

(71) Applicants: Niranjan Baisakh, Baton Rouge, LA (US); Venkata Ramanarao Mangu, Baton Rouge, LA (US)

(72) Inventors: Niranjan Baisakh, Baton Rouge, LA (US); Venkata Ramanarao Mangu, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 497 days.

(21) Appl. No.: 14/900,372

(22) PCT Filed: Jul. 7, 2014

(86) PCT No.: PCT/US2014/045527
§ 371 (c)(1),
(2) Date: Dec. 21, 2015

(87) PCT Pub. No.: WO2015/006185
PCT Pub. Date: Jan. 15, 2015

(65) Prior Publication Data
US 2016/0145637 A1    May 26, 2016

Related U.S. Application Data

(60) Provisional application No. 61/843,511, filed on Jul. 8, 2013.

(51) Int. Cl.
*C12N 15/82* (2006.01)
*A01G 22/00* (2018.01)

(52) U.S. Cl.
CPC ......... *C12N 15/8273* (2013.01); *A01G 22/00* (2018.02)

(58) Field of Classification Search
None
See application file for complete search history.

(56) References Cited

U.S. PATENT DOCUMENTS

| | | | |
|---|---|---|---|
| 2005/0044596 A1 | 2/2005 | Smith | 800/303 |
| 2005/0097639 A1 | 5/2005 | Nguyen et al. | 800/289 |
| 2007/0016976 A1 | 1/2007 | Katagiri et al. | 800/279 |
| 2008/0301839 A1* | 12/2008 | Ravanello | C07K 14/415 800/289 |
| 2009/0144848 A1 | 6/2009 | Kovalic et al. | 800/278 |
| 2010/0251424 A1 | 9/2010 | Conner et al. | 800/278 |
| 2011/0167514 A1* | 7/2011 | Brover | C07K 14/415 800/278 |

OTHER PUBLICATIONS

Huang et al. Comprehensive analysis of differentially expressed rice actin depolymerizing factor gene family and heterologous overexpression of OsADF3 confers *Arabidopsis thaliana* drought tolerance. Rice. 2012. 5:33. pp. 1-14.*
Schulze. Environment as stress factor: Stress physiology of plants. Plant Ecology. 2005. pp. 7-11.*
Jonak et al. Stress signaling in plants: A mitogen-activated protein kinase pathway is activated by cold and drought. Proc. Natl. Acad. Sci. 1996. 93: 11274-11279.*
Baisakh et al. Primary responses to salt stress in a halophyte, smooth cordgrass (*Spartina alterniflora* Loisel.). Functional & Integrative genomics. 2008. 8(3): 287-300.*
Subudhi et al. *Spartina alterniflora* Loisel., a halophyte grass model to dissect salt stress tolerance. In Vitro Cell Development Biology—Plant. 2011. 47: 441-457.*
Sengupta et al. An actin-depolymerizing factor from the halophyte smooth cordgrass, *Spartina alterniflora* (SaADF2), is superior to its rice homolog (OsADF2) in conferring drought and salt tolerance when constitutively overexpressed in rice. Plant Biotechnology Journal. 2019. 17: 188-205.*
Ali, G. et al., "Proteomic analysis of rice leaf sheath during drought stress," Journal of Proteome Reaseach, vol. 5, pp. 396-403 (2006).
Baisakh, N. et al., "cDNA-AFLP analysis reveals differential gene expression in response to salt stress in a halophyte *Spartina alterniflora* Loisel," Plant Science, vol. 170, pp. 1141-1149 (2006).
Baisakh, N. et al., "Primary responses to salt stress in a halophyte, smooth cordgrass (*Spartina alterniflora* Loisel.)," Functional & Integrative Genomics, vol. 8, pp. 287-300 (2008).
Baisakh, N. et al., "Heat stress alters the expression of salt stress induced genes in smooth cordgrass (*Spartina alterniflora* L.)," Plant Physiology and Biochemistry, vol. 47, pp. 232-235 (2009).
Baisakh, N. et al., "Enhanced salt stress tolerance of rice plants expressing a vacuolar $H^+$-ATPase subunit c1 (*SaVHAc1*) gene from the halophyte grass *Spartina alterniflora* Loisel," Plant Biotechnology Journal, vol. 10, pp. 453-464 (2012).
Bedre, R., "Genome-wide transcriptome analysis of the halophyte grass *Spartina alterniflora* reveals molecular basis of its salt adaptation responses," Plant and Animal Genome XXII, Abstract and Poster, Presentation #P795 (2014).
Datta, K. et al., "Overexpression of *Arabidopsis* and Rice stress genes' inducible transcription factor confers drought and salinity tolerance to rice," Plant Biotechnology Journal, vol. 10, pp. 579-586 (2012).

(Continued)

*Primary Examiner* — Ashley K Buran
(74) *Attorney, Agent, or Firm* — John H. Runnels

(57) ABSTRACT

Transformed plants are disclosed with enhanced resistance to abiotic stresses, such as salt stress, water stress, or temperature stress. Also disclosed are vectors useful for making such transformed plants, and methods of transforming plants to enhance resistance to abiotic stresses, such as salt stress, water stress, or temperature stress. For example, the *Spartina alterniflora* ADF gene SaADF2 enhances resistance when transformed into rice *Oryza sativa*. Transgenic rice plants that expressed higher levels of *Spartina* ADF were more resistant to salt, drought, and cold. There was improved growth, higher photosynthesis, and increased grain yield as compared to wild-type (WT) rice.

25 Claims, 8 Drawing Sheets
Specification includes a Sequence Listing.

(56) References Cited

OTHER PUBLICATIONS

Huang, Y. et al., "Comprehensive analysis of differentially expressed rice actin depolymerizing factor gene family and heterologous overexpression of OsADF3 confers *Arabidopsis thaliana* drought tolerance," The Rice Journal, vol. 5, No. 33 pp. 1-35 (2012).

Kasuga, M. et al., "Improving plant drought, salt, and freezing tolerance by gene transfer of a single stress-inducible transcription factor," Nature Biotechnology, vol. 17, pp. 287-291 (1999).

Ouellet, F. et al., "Regulation of a wheat actin-depolymerizing factor during cold acclimation," Plant Physiology, vol. 125, pp. 360-368 (2001).

Park, W. et al., "Genome-wide identification of differentially expressed genes under water deficit stress in upland cotton (*Gossypium hirsutum* L.)," BMC Plant Biology, 12:90 (2012).

Salekdeh, H. et al., "Proteomic analysis of rice leaves during drought stress and recovery," Proteomics, vol. 2, pp. 1131-1145 (2002).

Subudhi, P. "Spartina alterniflora root salinity induced expressed sequence tag (EST) Spartina alterniflora cDNA, mRNA sequence." *National Center of Biotechnology Information*. U.S. National Library of Medicine, Dec. 21, 2006. Web. 2008.

Wang, H. et al., "Down-regulation of GhADF1 gene expression affects cotton fibre properties," Plant Biotechnology Journal, vol. 6, pp. 1-11 (2008).

Yen, S. et al., "Proteomic analysis of salt stress-responsive proteins in rice root," Proteomics, vol. 5, pp. 235-244 (2005).

Zhang, H. et al., "Creating drought- and salt-tolerant cotton by overexpressing a vacuolar pyrophosphatase gene," Plant Signaling & Behavior, vol. 6, No. 6, pp. 861-863 (2011).

\* cited by examiner

```
  1 atggcttcatgcgcaccactccaatgcctctttctggtatggga
    M  A  F  M  R  T  H  S  N  A  S  S  G  M  G 46 gtcgctcctaacatcagggacacattccagcttcagatgaag
    V  A  P  N  I  R  D  T  F  H  E  L  Q  M  K 91 aaggcttccgatatgttatcttcaaaatcgaggaaaaacaaaag
    K  A  F  R  Y  V  I  F  K  I  E  E  K  Q  K 136 caggtggttgtggagaagactggggctactgaaagttatgat
    Q  V  V  E  K  T  G  A  T  E  S  Y  D 181 gacttttggcctccccagagaatgactgcagatgccctc
    D  F  L  A  S  L  P  E  N  D  C  R  Y  A  L 226 tatgattttgattttgttactggagaatgtgcagaaagcaag
    Y  D  F  D  F  V  T  G  E  N  V  Q  K  S  K 271 atattttcattgctggtctccattctacatcccggattcgtgct
    I  F  F  I  A  W  S  P  S  T  S  R  I  R  A 316 aagatgctgtactccacctccaaggatcgcatcaagcatgaactt
    K  M  L  Y  S  T  S  K  D  R  I  K  H  E  L 361 gatgggtttcactacgagatccaggcaacagattcatcagaggtg
    D  G  F  H  Y  E  I  Q  A  T  D  S  S  E  V 406 gacattgatgtgctccgagagcggggctcactga 438
    D  I  D  V  L  R  E  R  A  H  *
```

SEQ ID NO: 7

SEQ ID NO: 8

Fig. 1

ABIOTIC STRESS RESISTANCE

This is the United States national stage of international application PCT/US2014/045527, international filing date Jul. 7, 2014, which claims the benefit of the Jul. 8, 2013 filing date of U.S. provisional patent application Ser. No. 61/843,511 is claimed under 35 U.S.C. § 119(e). The complete disclosure of the priority application is hereby incorporated by reference in its entirety.

TECHNICAL FIELD

An actin depolymerizing factor from the halophyte grass *Spartina alterniflora* confers tolerance to multiple abiotic stresses, and is useful for transforming other plants (both monocots and dicots) to improve resistance to stress.

BACKGROUND ART

Drought, salinity, and extreme temperatures are the most common environmental stresses that adversely affect plant growth and development. These stresses limit plant productivity in cultivated areas worldwide. Under current, changing climate conditions, stress tolerance and crop yields under stress must be improved to supply food and fiber for an increasing world population.

Plants respond to abiotic stresses through various pathways. There is an unfilled need for improved stress tolerance in crops. Field crops, such as rice (*Oryza sativa* L.) or cotton (*Gossypium hirsutum* L.), typically experience more stress under similar conditions than do native plants growing wild in the same locale, for example native halophytes or native poikilohydric plants ("resurrection plants"). Rice plants, for example, are sensitive to salt, drought, and cold temperatures. Rice suffers from moderate to severe declines in both growth and productivity when exposed to drought or salt stress. Most rice plants grow poorly or not at all if the salt concentration is above ~50 mM NaCl, whereas the halophyte *Spartina alterniflora* (Loisel), also known as smooth cordgrass, can complete its entire life cycle under salinity as high as 500 mM NaCl. While cotton is generally more drought-tolerant than rice, high and consistent cotton yields are better achieved with supplemental irrigation in times of drought. Avoiding stress is particularly important during critical reproductive phases, and is one reason why over one-third of US cotton acreage is under some form of irrigation. External irrigation is costly. Additionally, the quality of available water for irrigation has declined in many locations, and available water is often higher in dissolved salts, which places additional stress on plants. Cotton fiber quality can decline when the plants suffer from drought or salinity stress.

In contrast to glycophytes (plants that are not salt-tolerant, such as rice or cotton), halophytes (salt-tolerant plants) have adaptations at physiological, cellular, and molecular levels that help the plants cope with higher salt concentrations. These mechanisms include ion homeostasis, osmotic adjustment, ion extrusion, and compartmentalization. *Spartina alterniflora* is a perennial deciduous grass, a halophyte that is native to intertidal saline marshes along the Atlantic coasts of North and South America, and the Gulf of Mexico. *S. alterniflora* is a facultative halophyte that accumulates $Na^+$, sequesters it in vacuoles, and excretes excess NaCl through specialized salt glands. *S. alterniflora* also synthesizes compatible solutes such as proline, glycine betaine; and it excludes ions from absorption by its roots. See Baisakh et al., *Plant Science* 170: 1141-1149 (2006). Identifying the genes responsible for stress tolerance in plants such as *S. alterniflora*, and transforming those genes into crop plants such as rice or cotton has the potential to create genetically modified crops with improved tolerance to abiotic stresses.

One way to improve the yields of cotton (or other crops) in drought and high salinity is to sequester cytosolic sodium into vacuoles, avoiding the accumulation of sodium ions at toxic levels in the cytoplasm, and achieving better water retention and higher salt tolerance. Vacuolar sodium sequestration is mediated by an active Na+/H+ "antiporter" membrane protein. The exchange of ions is driven by primary active $H^+$ transport at the vacuole by V-ATPase. (V-ATPase is an ATP-dependent protein pump.) $H^+$-ATPase acts as a primary transporter that pumps protons out of cytoplasm, creating pH and electric potential gradients across the vacuole membrane, thereby activating secondary transporters for ion and metabolite uptake. Baisakh et al., *Plant Biotechnology Journal* 10:453-464 (2012) reported that constitutive over-expression of a *Spartina alterniflora* gene (SaVHAc1) for c1 subunit vacuolar H+-ATPase gene conferred salt tolerance to transgenic rice plants.

Another approach to improving stress tolerance in field crops is to manipulate regulatory genes, such as those involved in signaling pathways, or transcription factors that modulate the downstream expression of stress-responsive genes. Park et al., BMC Plant Biology 12:90 (2012) recently identified a number of differentially-expressed mRNA transcripts in cotton plants subjected to water stress. Some of these transcripts were associated with heat shock and reactive oxygen species. Other researchers have identified dehydration-responsive element-binding genes, including DREB1 and DREB2. These genes are important in abscissic acid-independent stress tolerance pathways that interact with the cis-acting DRE (dehydration responsive element). Over-expression of the native form of DREB1 and of a constitutively-active form of DREB2 increases the tolerance of transgenic *Arabidopsis* plants to drought, salinity, and cold. Kasuga et al., Nature Biotechnology 17:287-291 (1999). Over-expression of DREB genes also increases tolerance of rice plants to salinity and drought. See Datta et al., *Plant Biotechnology Journal* 10:579-586 (2012).

The actin cytoskeleton is critical for many cellular processes, including several that are essential for plant development. These processes require constant reorganization and remodeling of the actin filament (F-actin) network. F-actin turnover involves polymerization, depolymerization, severing, nucleation, and large scale translocation events. The actin-binding proteins regulate the spatial configuration of actin arrays and dynamic cytoskeleton rearrangements. Actin-binding proteins sense environmental changes and influence actin filament polymerization, depolymerization, branching, and bundling.

Actin depolymerizing factor (ADF)/cofilins are a large family of ubiquitous, low molecular mass (15 to 20 kDa), actin-modulating proteins found in eukaryotic cells. As key regulators of the dynamics of actin arrays, these proteins play an important role in growth and development. ADF is phylogenetically conserved in plants, animals, and fungi. ADF specifically binds the actin-bound form of both monomeric (G-) and filamentous (F-) actin. ADF increases actin turnover by severing actin filaments, reducing filament length, and increasing barbed ends. ADF also increases dissociation of the F-actin monomer from the pointed ends by changing the helical twist of the actin filament, thereby accelerating the dissociation of actin subunits. Reversible phosphorylation, specific phosphoinositides, calcium-stimulated protein kinase, Rop GTPases, and pH all affect ADF activity in plants. ADFs also play a role in pollen tube growth, root formation, and cold acclimation.

Yan et al., *Proteomics* 5:235-244 (2005) reported a systematic proteomic investigations of salt stress-responsive proteins in rice. One of the proteins up-regulated following salt stress was identified as a putative actin-binding protein, that the authors suggested was probably a previously unreported ADF in rice.

Studying the regulation of plant ADF has been challenging because of the presence of numerous isoforms in higher plants. RNAi-mediated knockdown of ADF2 has been reported to interfere with cell growth and differentiation in *Arabidopsis*. Mass spectrometry showed up-regulation of ADF proteins in rice leaves after 23 days of water stress. See Salekdeh et al., *Proteomics* 2:1131-1145 (2002).

Ali and Komatsu, *Journal of Proteomics Research* 5:396-403 (2006) reported that ADF was up-regulated in rice leaf sheath after 2 to 6 days of drought stress. See also www.ncbi.nlm.nih.gov/nucest/EH277804.

Baisakh et al., *Functional & Integrative Genomics* 8:287-300 (2008) reported that an ADF-like protein was up-regulated in *S. alterniflora* under salt stress.

Ouellet et al., *Plant Physiology* 125:360-368 (2001) reported that ADF was up-regulated in wheat (*Triticum aestivum*) during cold stress.

Baisakh and Subudhi, *Plant Biotech J.* 47:232-235 (2009) reported down-regulation of ADF in leaves and a slight up-regulation in roots under heat stress in *S. alterniflora*

Huang et al., *The Rice J.* 5:33: 1-35 (2012) reported that ADF3 was up-regulated in rice under drought stress. Overexpression of rice ADF3 was reported to confer drought tolerance to *Arabidopsis*.

Increased expression of an *Arabidopsis* vacuolar pyrophosphatase gene, AVP1, was reported to enhance drought and salt tolerance in transgenic cotton. (Zhang et al., *Plant Signaling & Behavior* 6:861-863 (2011). The likely molecular mechanism of AVP1-mediated drought resistance was described as increased proton pump activity in vacuolar pyrophosphatase, which increases the proton electrochemical gradient across the vacuolar membrane. This gradient leads both to lower water potential in the plant vacuole and to higher secondary transporter activities, inhibiting toxic ion accumulation in the cytoplasm. Overexpression of AVP1 appeared to stimulate root development, and the larger root system allowed AVP1-overexpressing plants to absorb water more efficiently under drought and saline conditions, enhancing stress tolerance and increasing yields. Larger root systems or shifts in root/shoot ratio could improve cotton yields under water stress conditions.

Bedre et al., "Genome-wide transcriptome analysis of the halophyte grass *Spartina alterniflora* reveals molecular basis of its salt adaptation responses, Abstract and Poster, presentation # P795 at the Plant and Animal Genome XXII meeting, (Jan. 11-14, 2014, San Diego, Calif.) describes findings for leaf and root transcriptome analysis of *Spartina alterniflora* subjected to 500 mM NaCl.

Climate change can lead to unpredictable weather patterns, rises in sea level and saltwater incursions (salinity stress), erratic rainfall (water stress), and temperature fluctuations (cold and heat stress). These environmental stresses can adversely affect crop growth and productivity. There is an unfilled need for improved field crops that can better tolerate such abiotic stresses.

DISCLOSURE OF THE INVENTION

We have discovered transformed plants with enhanced resistance to abiotic stresses, such as water stress, salt stress, or temperature stress. We have also discovered vectors useful for making such transformed plants, and methods of transforming plants to enhance resistance to abiotic stresses, such as water stress, salt stress, or temperature stress. For example, the *Spartina alterniflora* ADF gene SaADF2 enhances resistance when transformed into rice (*Oryza sativa*). Transgenic rice plants that expressed higher levels of the ADF were more resistant to drought, salt, and cold. There was improved growth, higher photosynthesis, and increased grain yield as compared to wild-type (WT) rice.

In one embodiment, a DNA sequence encoding ADF was cloned from the halophyte *S. alterniflora*, which is known to tolerate multiple abiotic stresses. "Gene silencing" was not observed in our experiments when the orthologous gene from *S. alterniflora* was expressed in rice. The exogenous gene continued to be expressed, and continued to provide resistance to stress, in future generations of rice plants. (To date, heritability has been demonstrated through the $T_4$ generation.)

We isolated and identified a cDNA from *S. alterniflora* that showed significant homology to ADF genes from other plants. We found that this gene, "SaADF2," was strongly up-regulated in *S. alterniflora* under salt or drought stress. The cDNA contained a 438 base open reading frame that we predicted to encode a membrane protein with 145 amino acid residues (three α-helices and six β-strands). Amino acid residues 19 to 145 were the ADF/cofilin domain.

The halophyte SaADF2 gene conferred increased tolerance to drought, salinity, and temperature stresses when transformed into rice (a monocot) and *Arabidopsis* (a dicot).

We successfully introduced SaADF2 DNA into a *japonica* rice genotype, Nipponbare, under the control of the 35S cauliflower mosaic virus constitutive promoter. Rice plants were transformed by *Agrobacterium tumefaciens*, following the protocol otherwise described in Rao et al., *Plant Cell Tissue and Organ Culture* 99:277-285 (2009). By contrast, overexpressing the corresponding rice ortholog, OsADF2, did not result in a comparable improvement in stress.

Drought experiments proved that transgenic rice plants homozygous for SaADF2 were highly tolerant to low-water conditions. The SaADF2 transgenic rice plants showed no signs of wilting until 11 to 14 days of drought stress, compared to WT plants that showed leaf rolling and drying after only 4 to 5 days without water. The transgenic rice showed improved shoot and root growth, maintained higher relative water content (RWC), and had higher proline and stomatal photosynthetic yield compared to WT rice. These observations held true during both the vegetative and reproductive stages under drought conditions. At harvest, the transgenic grain yield was 3 to 4 times higher than that for WT rice.

In salinity experiments, the introduced gene conferred increased tolerance to salt stress (150 mM NaCl) under hydroponic conditions. The transgenic plants showed less leaf tip burning, less yellowing, and less damage to Photosystem II. They also had higher chlorophyll and higher water content as compared to WT plants.

In experiments with cold stress, SaADF2 transgenic rice tolerated one week at 4° C., while WT plants had rolled and dried leaves and ultimately died after one week.

The SaADF2 gene may be used to transform plants and enhance stress resistance in both monocots (rice, corn, sugarcane, wheat, etc) and dicots (cotton, soybean, canola etc). Transformed plants will better tolerate abiotic stresses including water, salt, and temperature stress.

BRIEF DESCRIPTION OF THE DRAWINGS

FIG. 1 depicts the nucleotide (SEQ ID NO:7) and inferred amino acid (SEQ ID NO:8) sequences of SaADF2.

MODES FOR CARRYING OUT THE INVENTION

Methods

TABLE 1

Figure 2:
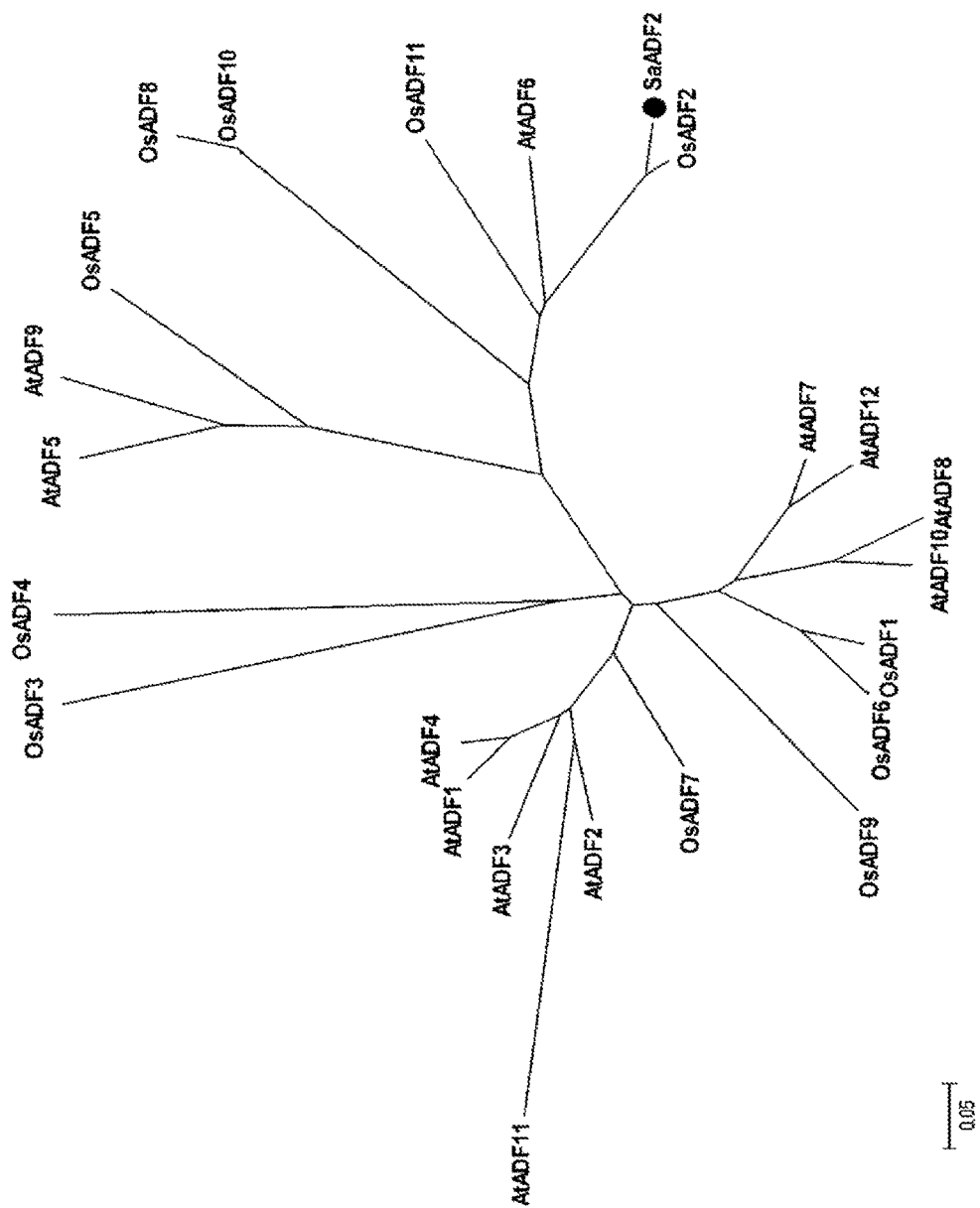
FIG. 2 depicts a phylogenetic tree showing inferred relationships among different ADF proteins from *S. alterniflora*, *O. sativa*, and *Arabidopsis*.

| Abbreviations | |
|---|---|
| ADF | Actin depolymerizing factor |
| EST | Expressed sequence tag |
| RWC | Relative water content |
| WT | Wild-type |

Example 1

RNA Isolation and cDNA Synthesis

Synthetic sea salts (Instant Ocean, Aquarium Systems, Mentor, Ohio) at 5% (w/v) were used to impose stress on *S. alterniflora* plants in a greenhouse, using the procedure otherwise described in Baisakh et al., *Functional and Integrative Genomics*, 8:287-300 (2008). Total RNA was isolated from freshly harvested leaves of both stressed and unstressed *S. alterniflora* after 24 h, 48 h, 72 h, 96 h, and 1 week. An RNeasy plant mini-kit (Qiagen, USA) was used, following the manufacturer's instructions. Total RNA was measured for quality control purposes, using 1.2% formamide-denaturing agarose gel electrophoresis and an ND-1000 spectrophotometer (Nanodrop Technologies, Wilmington, Del.). cDNA was synthesized from 1 µg RNA using an iScript™ cDNA synthesis kit (Bio-Rad, USA) following the procedure otherwise described in Baisakh et al., *Plant Biotechnology Journal* 10:453-464 (2012).

Example 2

Cloning, Sequence Analysis, and Binary Vector Construction

Genome-wide transcriptome profiling was performed to identify putative abiotic stress-response genes from *Spartina alterniflora*, using National Center for Biotechnology Information (NCBI) BLAST software: BLASTP compares an amino acid query sequence against a protein sequence database. BLASTN compares a nucleotide query sequence against a nucleotide sequence database. BLASTX compares a nucleotide query sequence, translated in all reading frames, against a protein sequence database.

Polymerase chain reaction (PCR) primers were designed from an expressed sequence tag showing similarity to plant ADF sequences, when compared to the non-redundant nucleotide database (BLASTN) and to the protein database (BLASTP). The complete open reading frame of SaADF2 was amplified from the first strand cDNA of *S. alterniflora* by PCR using primers SaADF2 Fwd: 5'-GGAAGATC-TATGGCCTTCATGCGCAC-3' (SEQ ID NO: 1) and SaADF2 Rev: 5'-GGGTAACCTCAGTGAGCCCGCTC-3' (SEQ ID NO: 2), which contain Bgl II and BstE II restriction sites, respectively.

Construction of p35S::SaADF2 in a pCAMBIA1305.1 plant expression vector, and its subsequent incorporation into *Agrobacterium tumefaciens* LBA4404 cells were performed as otherwise described in Baisakh et al., *Plant Biotechnology Journal* 10:453-464 (2012). The identity and orientation of p35S:SaADF2 was confirmed by restriction digestion and sequencing. FIG. 1 depicts the observed nucleotide and inferred amino acid sequences of SaADF2. Nucleotides 1-3 (ATG) are the start codon, and nucleotides 436-438 (TGA) are a stop codon. The rectangular box in FIG. 1 represents the ADF-H domain of actin depolymerizing factor (as inferred by sequence homology with other plant ADFs).

Nucleotide and protein sequences similar to SaADF2 were retrieved from NCBI and UniprotKB databases. SaADF2 and its orthologs from various organisms were aligned using Clustal Omega software. Phylogenetic analysis was performed in Phylogeny.fr and TreeDyn, using the neighbor-joining method, on www.phylogeny.fr/version2_cgi/index.cgi.

Example 3

Rice Transformation

Embryogenic rice calli, cultivar 'Nipponbare,' were transformed with SaADF2-containing *Agrobacterium tumefaciens*. Primary transformed ($T_0$) lines were screened by PCR, using both SaADF2-specific and hygromycin phosphotransferase (hpt, a selectable marker)-specific primers. Transgenic lines were advanced to the $T_2$ generation via self-pollination to obtain homozygous lines.

Example 4

Molecular Analysis of Plants Expressing SaADF2

Total genomic DNA was isolated from rice leaf tissues using a modified CTAB method, and was quantified with a NanoDrop Spectrophotometer (ND1000, Wilmington, USA). One hundred ng of DNA was analyzed by PCR for both a selectable marker gene (hpt) and the target gene (SaADF2) using gene-specific primers (5'-3') as follows: HPT Fwd: tacttctacacagccatc (SEQ ID NO:3), HPT Rev: tatgtcctgcgggtaaat (SEQ ID NO:4); SaADF2 Fwd: ATC-GAGGAAAAGCAAAAGCA (SEQ ID NO:5), SaADF2 Rev: CGATCCTTGGAGGTGGAGTA (SEQ ID NO:6).

Total RNA was extracted from 100 mg of freshly collected leaf and root tissues of SaADF2 and WT rice after 0 h, 12 h, 24 h, 36 h, and 48 h of drought stress. Two micrograms of total RNA were analyzed by semi-quantitative reverse transcription polymerase chain reaction (RT-PCR) amplification of the SaADF2 gene, employing a single-step RT-PCR kit (Qiagen, Valencia, Calif.). The products were resolved in 1.0% TAE agarose gel, and visualized under a UV transilluminator in a Kodak 200 gel doc apparatus (Carestream Health, Inc., Rochester, N.Y.). The rice actin 1 gene was used as an internal control for template validation.

Example 5

Salinity and Drought Tolerance Assay in Rice

Eight independent transgenic rice lines SaADF2 #2, SaADF2 #13 and SaADF2 #23, SaADF2 #31, SaADF2 #35, SaADF2 #38, SaADF2 #41 and SaADF2 #42 (i.e., lines derived from eight independent transformation events) were used for salt and drought stress. SaADF2 #2 and SaADF2 #31 were used for cold stress experiments. (data not shown).

Note: The nomenclature seen in some of the figures such as 31-4-8-12-7 describes the lineage. In this example, "31" refers to the $31^{st}$ $T_0$ transgenic plant, the "4" refers to the $4^{th}$ plant in the $T_1$ generation; the "8" refers to the $8^{th}$ plant in the $T_2$ generation, etc.

Three-week-old homozygous SaADF2 and WT rice seedlings (grown hydroponically in Yoshida's nutrient solution) were subjected to salt stress (150 mM NaCl) for one week. The floating leaf disk assay was used to determine chlorophyll bleaching as a measure of salt tolerance.

Drought stress was imposed on 45 day-old SaADF2 rice lines and WT rice. Both were grown for 14 d (without irrigation) in deep plastic pots inside a greenhouse, maintained at 29° C. (day) and 21° C. (night) with 14 h of daylight and 10 h of darkness per day. Each pot had a single plant. The stress treatment was applied (the plants were not watered), and soil moisture content was recorded every two days.

Example 6

Physiological Analysis

Volumetric soil moisture content is the ratio of the volume of water present to the total volume of the sample. Soil moisture sensors respond to the soil dielectric constant ε, which depends strongly on water content. The volumetric soil moisture content ($\theta_v$, $m^3$ $m^{-3}$) was measured at room temperature with a portable HH2 Moisture Meter (Delta-T Devices Ltd., England, U.K.) using a Theta probe ML2x.

Stomatal conductance is a measure of the rate of carbon dioxide ($CO_2$) or water vapor passage through the stomata of a leaf. Stomata conductance (mmol $m^{-2}s^{-1}$) was measured using a Leaf Porometer (Decagon Devices Inc., Pullman, Wash.).

Relative water content (RWC) of leaves (actual water content as a fraction of the fully hydrated water content) was determined using the method otherwise described in Baisakh et al., *Plant Biotechnology Journal* 10:453-464 (2012).

Chlorophyll fluorescence was measured at room temperature with a portable fluorometer (PAM-2100; Walz, Germany). The minimum fluorescence level (Fo), with all photosystem II reaction centers open, was determined by measuring modulated light, at a sufficiently low level. The maximum fluorescence level (Fm), with all photosystem II reaction centers closed, was determined with a 0.8 s saturating pulse in dark-adapted leaves. Photosynthetic yield was determined as: photosynthetic yield=1.0–Fo/Fm.

Results

Example 7

Sequence Analysis of SaADF2

An expressed sequenced tag (EST) from *S. alterniflora* containing a 438 bp open reading frame was identified. A homology search (with BLASTx and BLASTn) against the NCBI protein and nucleotide databases and the UniprotKB database showed the cDNA to be similar to ADF from other plants. We named the gene SaADF2, and predicted it to be a membrane protein containing 145 amino acid residues (FIG. 1).

Comparative sequence analysis of SaADF2 versus orthologs from other species showed that the SaADF2 open reading frame shared more than 90% similarity with ADF from several grasses: rice ADF2 (OsADF2), *Zea mays* ADF6 (ZmADF6), and *Brachypodium distachyon* ADF2 (BdADF2). Other monocot and dicot species whose ADF shared significant similarity with SaADF2 included: *Arabidopsis thaliana* (AtADF6), *Gossypium hirsutum* (GhADF4), *Glycine max* (GmADF), *Vitis vinifera* (VvADF), *Sorghum bicolor* (SbADF), *Ricinus communis* (RcADF), *Solanum tuberosum* (StADF6), and *Populus trichocarpa* (PtADF1). Similarly, protein sequence analysis comparing SaADF2 with several members of the ADF family from rice and *Arabidopsis thaliana* showed that SaADF2 was most similar to OsADF2 from rice.

FIG. 2 depicts a phylogenetic tree of predicted relationships among several members of the ADF family from *S. alterniflora, O. sativa*, and *A. thaliana*. The radial tree was constructed using the neighbor-joining algorithm, and was subjected to a bootstrap test with 1000 iterations. UniprotKB accession numbers of the *Oryza sativa* (Os) and *Arabidopsis thaliana* (At) ADF proteins were OsADF1: Q6EUH7; OsADF2: Q9AY76; OsADF3: Q84TB6; OsADF4: Q84TB3; OsADF5: Q10P87; OsADF6: Q7XSN9; OsADF7: Q0DLA3; OsADF8: Q0D744; OsADF9: Q8H2P8; OsADF10: Q337A5; OsADF11: Q2QLT8; AtADF1: Q39250; AtADF2: Q39251; AtADF3: Q9ZSK4; AtADF4: Q9ZSK3; AtADF5: Q9ZNT3; AtADF6: Q9ZSK2; AtADF7: Q67ZM4; AtADF8: Q570Y6; AtADF9: O49606; AtADF10: Q9LQ81; AtADF11: Q9LZT3; and AtADF12: Q8LFH6.

Domain analysis of the 145 amino acid sequence of SaADF2 predicted a Cofilin/ADF (ADF-H domain) from amino acids 19 to 145, a domain that is highly conserved across plant species. Homology model-based analysis of probable tertiary and secondary structures suggested that SaADF2 contains three α-helices and six β-strands.

Example 8

Stable Integration and Inheritance of SaADF2 in Transgenic Rice

Figure 3:
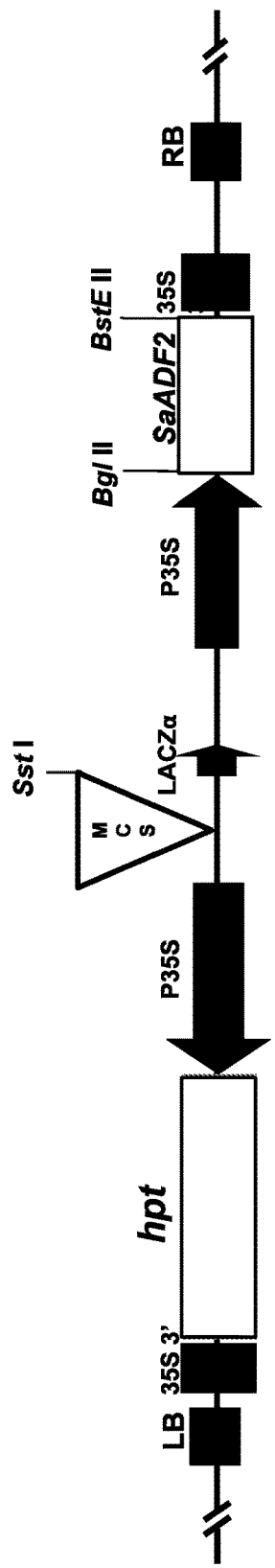
FIG. 3 depicts the T-DNA structure of the p35S::SaADF2 vector used for rice transformation.

Thirty-two transformants were confirmed positive for integration of the SaADF2 expression cassette through PCR analysis using gene-specific primers. These plants were grown to maturity in the greenhouse. T1 progeny analysis showed eight independent transgenic lines (SaADF2 #2, SaADF2 #13 and SaADF2 #23, SaADF2 #31, SaADF2 #35, SaADF2 #38, SaADF2 #41, and SaADF2 #42) with single copy gene integration at a 3:1 segregation ratio. (I.e., there were eight independent transformation events; and thirty-two lines were derived from those eight events.) FIG. 3 depicts the T-DNA (*Agrobacterium* transferred DNA) structure of the p35S::SaADF2 vector used for rice transformation. The following table identifies components of FIG. 3.

TABLE 2

Components of p35S::SaADF2

| | |
|---|---|
| LB | Left border |
| 35S 3' | 35S terminator sequence |
| hpt | hygromycin phosphotransferase selectable marker |
| P35S | CaMV 35S promoter |
| MCS | Multi-cloning site |
| LACZa | lac operon |
| SaADF2 | actin depolymerizing factor 2 gene from *S. alterniflora* |
| RB | Right border |

Example 9

SaADF2 Expression Conferred Salt Tolerance

Floating leaf disc assays of transgenic and WT rice plants showed clear differences in chlorophyll loss under salt stress (150 mM NaCl). Under salt stress the WT plants suffered high bleaching, and more leaf rolling, withering, tip burning, and dye-back symptoms than did the transgenic plants. In addition, WT plant growth was inhibited far more than that the transgenic rice plants, as evidenced by shoot and root lengths after a week of salty conditions.

Under non-stress (control) conditions, the growth and development of transgenic and WT rice seedlings were essentially indistinguishable. However, ADF2 expression was higher in the transgenic plants than in the WT plants, even under control conditions (as assayed by RT-PCR)—which was expected because the SaADF2 gene was under the control of a constitutive promoter (CaMV 35S). Furthermore, the transgenic plants maintained higher ADF2 expression in their leaves and roots through 48 h of salt stress, while ADF2 accumulation was significantly reduced in WT plants. There was a transient up-regulation of ADF2 after 12 h of salt stress in both the transgenic plants and the wild-type plants.

Example 10

SaADF2 Overexpression Improved Drought Tolerance

When rice plants were subjected to drought conditions during a vegetative-reproductive transition stage, the SaADF2-transgenic plants were more tolerant to water stress than were the WT plants. The WT plants showed leaf rolling by day 4, and were completely dry and withered by day 14. Growth was also severely inhibited. These plants showed early senescence due to severe loss of chlorophyll. By contrast, the transgenic plants did not show leaf-rolling and the onset of growth inhibition until day 11. The transgenic plants stayed green longer, and delayed the onset of senescence.

Plant recovery after drought conditions was measured by first depriving plants of water for 11 d or 14 d, and then resuming 4 d of normal watering. After 14 d of water stress, the WT plants never recovered, although the transgenic plants recovered to normal growth within about one week. After 11 d of water stress, both transgenic and WT plants recovered; however, the growth of transgenic rice was thereafter significantly higher than the WT rice, which flowered late with a poor seed set. Ground biomass and root growth were measured following drought stress and the transgenic rice again fared better than the WT rice. (See FIGS. 8A and 8B.)

Figure 4:
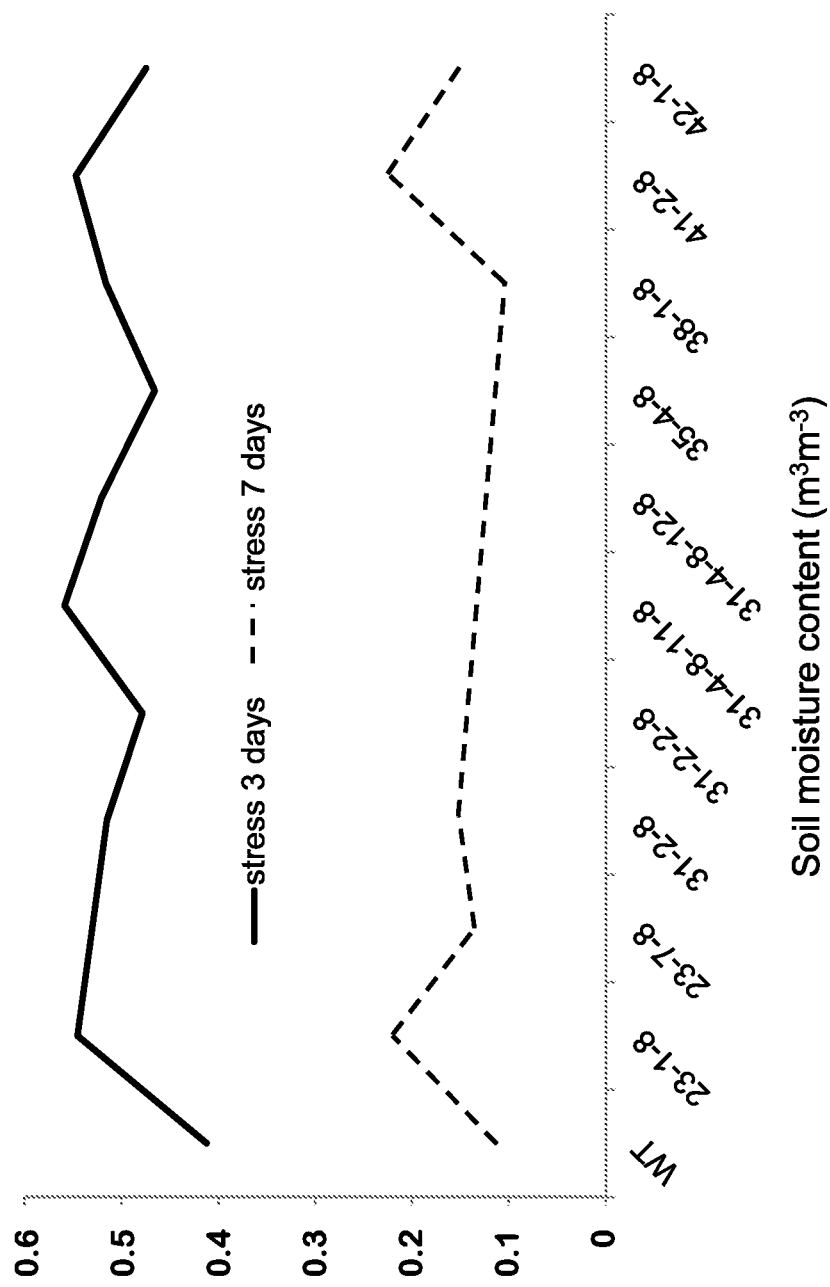
FIG. 4 depicts measured soil moisture content for experimental plants after 3 days and 7 days.

It was also observed that soil moisture in the pots with the transgenic lines was generally higher (average 0.15 $m^3/m^3$) than those with the WT rice (0.113 $m^3/m^3$) (FIG. 4). These observations indicated that the transgenic plants used water more efficiently, leading to prolonged survival under continuing drought stress.

Example 11

Stomata Conductance and Relative Water Content

Figure 5:
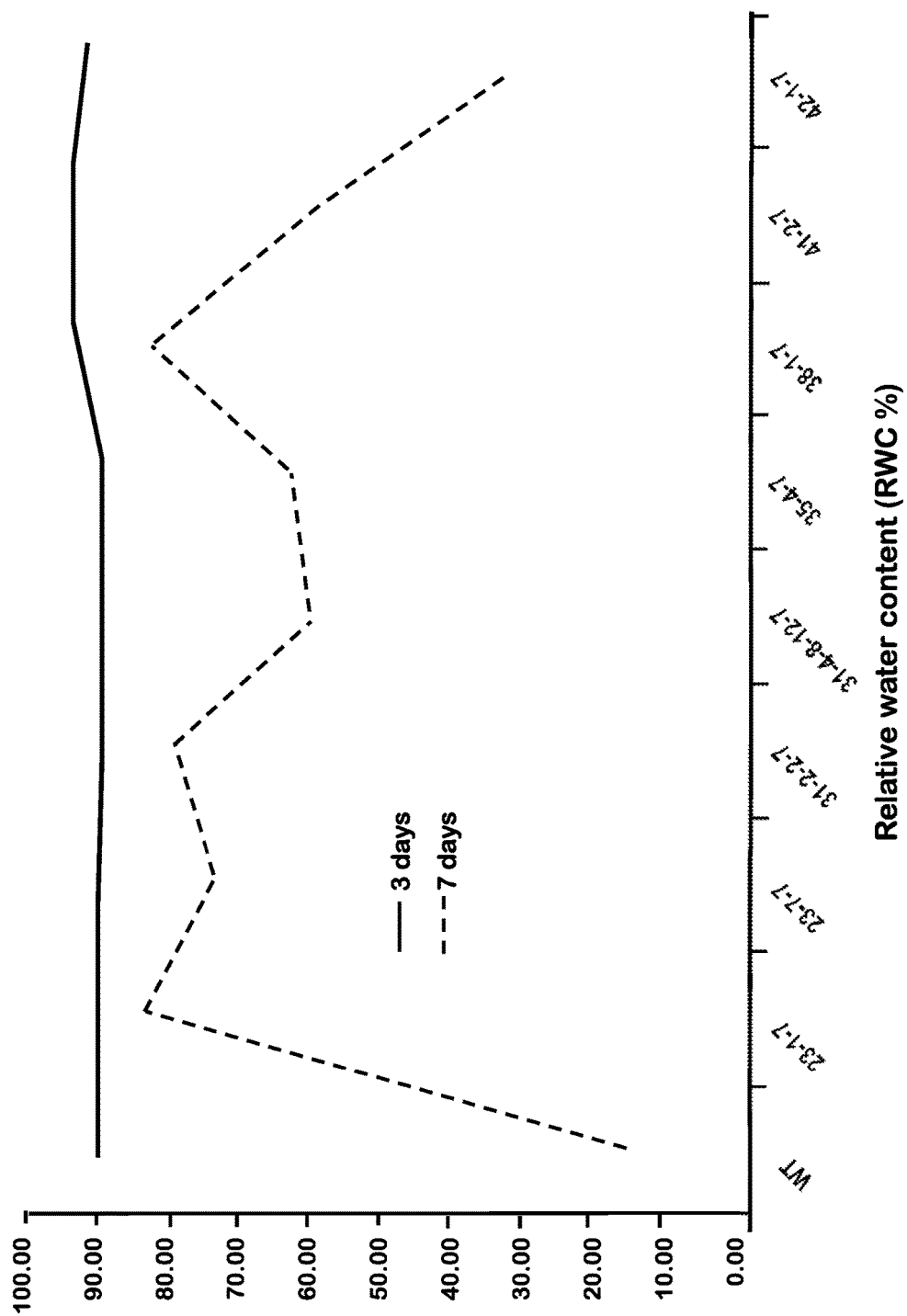
FIG. 5 depicts the relative water content in the plant leaves after 3 days and 7 days of drought conditions.

Transgenic plants had better osmotic adjustment under water stress than did WT plants, as shown by their much higher relative water content (RWC). The WT plants lost 84% RWC in leaves after one week of drought. The transgenic lines lost an average of 28% RWC in leaves over the same time. FIG. 5 depicts RWC in transgenic and WT leaves after 3 days and 7 days of drought. Because the transgenic plants maintained higher RWC than the WT, they had less tissue damage under drought conditions.

Figure 6:
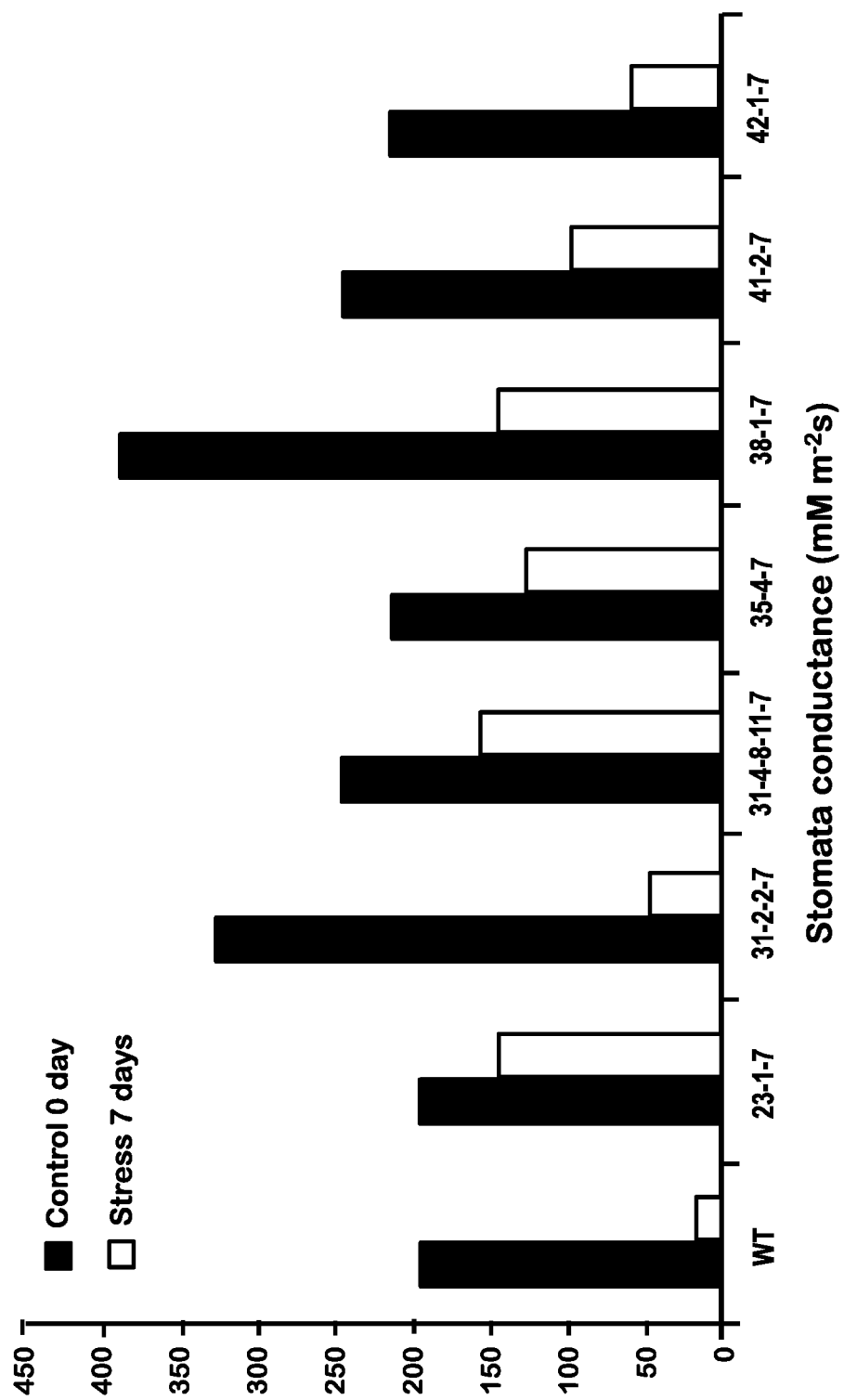
FIG. 6 depicts stomata conductance, a measure of transpiration loss, for control plants and drought-stressed plants.

The transgenic plants had generally higher stomata conductance than WT plants under non-stress control conditions. As the lack of water increased stress on the plants, there was a general decline in the transpiration rate. Although the stomata conductance of all plants was reduced substantially, the transgenic lines showed less reduction than did the WT plants. FIG. 6 shows stomata conductance as a measure of transpiration loss under drought stress after 0 days and 7 days of drought, for both WT and transgenic plants.

Example 12

Photosynthetic Yield

Figure 7:
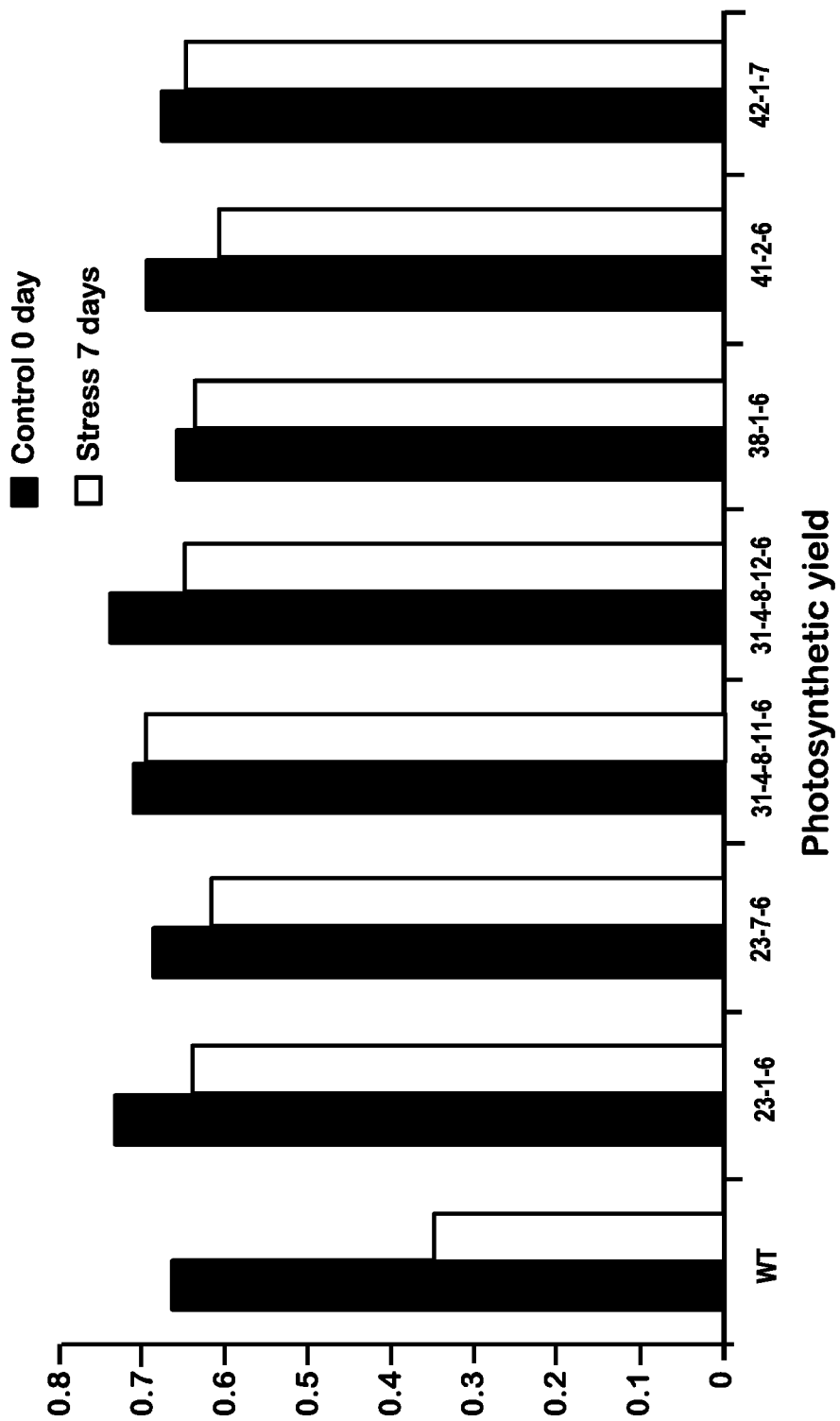
FIG. 7 depicts photosynthetic yields for control plants and drought-stressed plants.

Under drought stress conditions, the transgenic rice plants maintained substantially higher levels of photosynthesis than did WT plants. The transgenic plants maintained higher photosystem II efficiency, which enhanced chlorophyll 'a' levels. FIG. 7 depicts a much higher photosynthetic yield in transgenic lines compared to WT under drought stress. We also observed less reduction in chlorophyll fluorescence, indicating that SaADF2 overexpression led to protection of photosystem II in transgenic rice under water stress conditions.

Accumulation of the ADF2 mRNA transcript was much higher in the SaADF2-transgenic rice plants under both control and water-stressed conditions, as determined by semi-quantitative RT-PCR. Interestingly, the transcript level was very high after 7 d of stress in the transgenic plants, as compared to levels after only 1 d or 3 d of water stress. Rice elongation factor 1a (OsEF1a) was used as the internal control. (Data not shown.)

Example 13

Grain Production

The transgenic rice lines had higher photosynthesis levels than did WT plants under stress conditions. The transgenic rice lines stayed green longer, had higher RWC, and suffered lower stress-induced photosynthesis inhibition. These traits contributed to significantly higher grain yields and biomass yields for the drought-stressed transgenic plants as compared to WT plants. Under stress, WT grain yield dropped by 85%, whereas grain yield for transgenic rice dropped by an average of only 24% (range: 21% to 27%). Similarly, WT biomass yield declined 69% loss, while transgenic biomass declined an average of 37% (range: 23% to 42%).

Figures 8A, 8B:
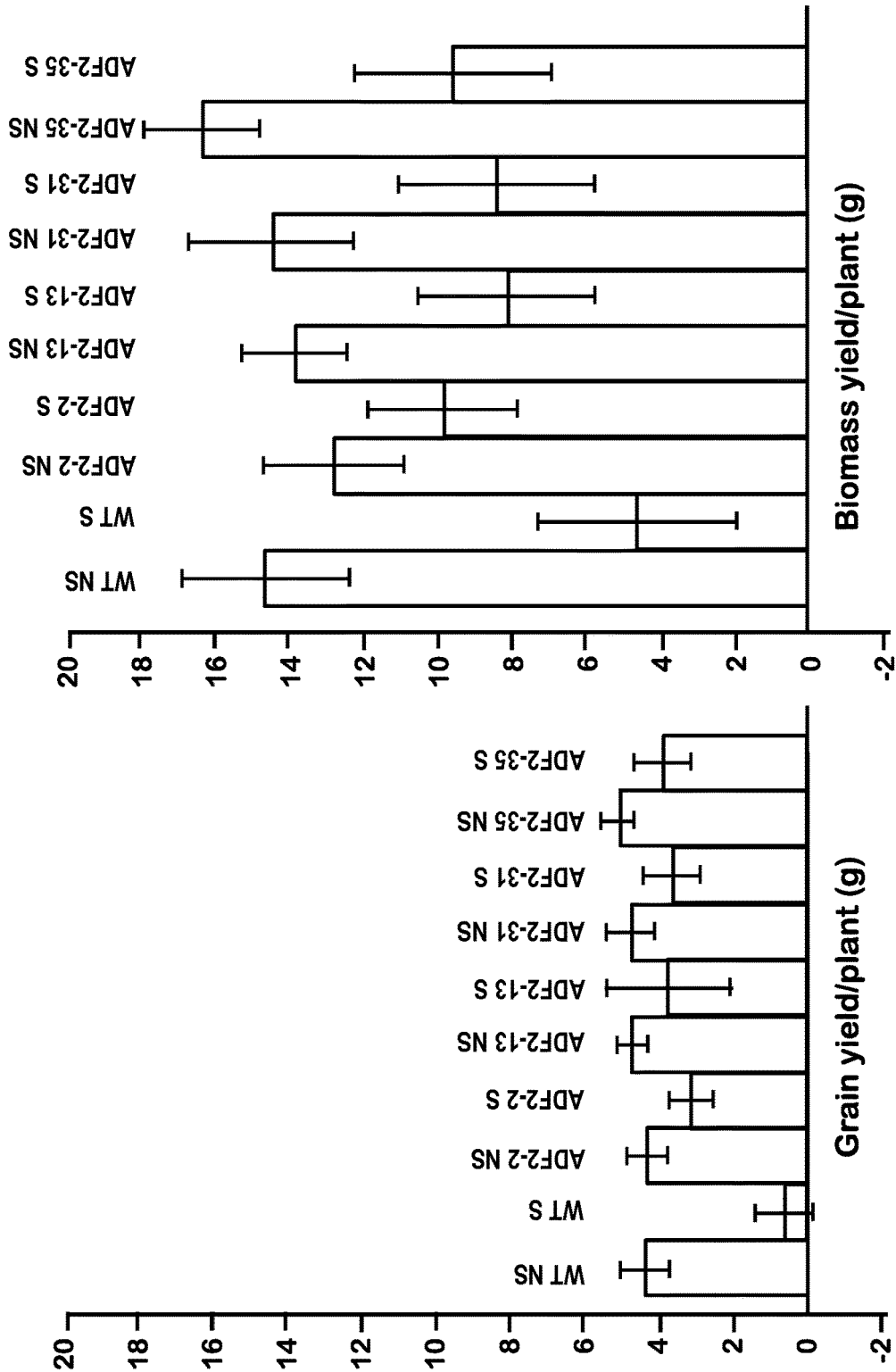
FIGS. 8A and 8B depict grain yield and biomass yield, respectively, following drought stress in both transgenic and wild-type rice.

FIGS. 8A and 8B depict per-plant grain and biomass yields, respectively, for transgenic and WT rice, with and without drought stress. Grain yields of transgenic and WT rice were comparable in the absence of stress.

Transgenic rice lines tolerated cold stress better than WT plants, as measured by growth and development, after 3 d and 7 d of exposure to 4° C. Physiological analyses of transgenic response to stress as compared to that of WT under salt or cold stress gave similar results to those seen for drought stress (data not shown).

Example 14

Dicot Transformation

To confirm the effectiveness of the SaADF2 gene and protein not only in monocots but also in dicots as well, the SaADF2 gene was also transformed into *Arabidopsis* with the *Agrobacterium* vector. Preliminary results indicated that *Arabidopsis* transgenic plants (AtOx) overexpressed SaADF2, and had increased tolerance to drought and salt stress in the vegetative and reproductive stages as compared to WT plants. (data not shown)

Example 15

Inducible Promoter from *Spartina alterniflora*

We have also placed the SaADF2 coding sequence under the control of a native *Spartina alterniflora* promoter for abscissic acid stress ripening protein (SaAsr1), SEQ ID NO:9. The promoter is described in Subudhi and Baisakh, In vitro *Cellular and Developmental Biology—Plant* 47:441-457 (2011). The fusion construct was transformed into and tested in *Arabidopsis*. The transgenic *Arabidopsis* plants expressing SaADF2 under the control of SaAsr1 promoter showed slightly better root and shoot growth under 150 mM NaCl salt stress when compared to those in which the SaADF2 gene was controlled by the CaMV 35S constitutive promoter (data not shown).

Example 16

Additional Transformations

The vector disclosed here may be used to transform the SaADF2 gene into any crop of interest, monocot or dicot, to improve tolerance to stress. Representative crops into which the SaADF2 gene will be transformed include rice, wheat, soybeans, maize, tomatoes, sugarcane, potatoes, grapes, cotton, and others.

DEPOSIT INFORMATION

A sample of the p35S::SaADF2 vector containing the SaADF2 gene was deposited with the American Type Culture Collection (ATCC), 10801 University Boulevard, Manassas, Va. 20110-2209 on 1 Jul. 2014, and was assigned ATCC Accession No. PTA-121363. This deposit was made under the Budapest Treaty.

Cloning into Other Green Plants.

The SaADF2 gene may be used to transform the stress tolerance trait into green plants generally. Stress tolerance may be then introduced into other allospecific or conspecific plants, for example, either by traditional breeding, back-crossing, and selection; or by transforming cultivars with the cloned nucleotide sequences. Direct transformation of cultivars has the potential to allow quick introduction of the resistance characteristics into a variety, without requiring multiple generations of breeding and back-crossing to attain uniformity.

It will be understood by those skilled in the art that the listed nucleic acid sequences are not the only sequences that can be used to confer stress tolerance. Also contemplated are those nucleic acid sequences that encode identical but that, because of the degeneracy of the genetic code, possess different nucleotide sequences. For example, it is well known in the art that the codon for asparagine may be either AAT (AAU) or AAC.

The invention also encompasses nucleotide sequences encoding peptides or proteins having one or more silent amino acid changes in portions of the molecule not directly involved with stress tolerance. For example, alterations in the nucleotide sequence that result in the production of a chemically equivalent amino acid at a given site are contemplated; thus, a codon for the amino acid alanine, a hydrophobic amino acid, may be substituted by a codon encoding another hydrophobic residue, such as glycine, or may be substituted with a more hydrophobic residue such as valine, leucine, or isoleucine. Similarly, changes that result in the substitution of one negatively-charged residue for another, such as aspartic acid for glutamic acid, or one positively-charged residue for another, such as lysine for arginine, can also be expected to produce a biologically equivalent product.

This invention relates not only to a functional SaADF2 sequence as described in this specification, but also to proteins having modifications to such a sequence resulting in an amino acid sequence having the same function (i.e., a functional ADF imparting stress tolerance), and about 60-70%, preferably 90% or greater homology to the sequence of the amino acid sequence as described, more preferably about 95% or greater homology. "Homology" as used here means identical amino acids or conservative substitutions (e.g., acidic for acidic, basic for basic, polar for polar, nonpolar for nonpolar, aromatic for aromatic). The degree of homology can be determined by simple alignment based on programs known in the art, such as, for example, GAP and PILEUP by GCG, or the BLAST software available through the NIH internet site. Most preferably, a certain percentage of "homology" would be that percentage of identical amino acids.

A particular desired point mutation may be introduced into a coding sequence using site-directed mutagenesis methods known in the art. Isolated DNA sequences of the present invention are useful to transform target crop plants or ornamental plants, and thereby confer stress tolerance. A broad range of techniques currently exists for achieving the direct or indirect transformation of higher plants with exogenous DNA, and any method by which one of the SaADF2 sequences can be incorporated into the host genome, and stably inherited by its progeny, is contemplated by the present invention.

Transformation of plant cells can be mediated by the use of vectors. A common method for transforming plants is the use of *Agrobacterium tumefaciens* to introduce a foreign nucleotide sequence into the target plant cell. For example, a SaADF2 nucleotide sequence is inserted into a plasmid vector containing the flanking sequences in the Ti-plasmid T-DNA. The plasmid is then transformed into *E. coli*. A triparental mating is carried out among this strain, an *Agrobacterium* strain containing a disarmed Ti-plasmid containing the virulence functions needed to effect transfer of the SaADF2-containing T-DNA sequences into the target plant chromosome, and a second *E. coli* strain containing a plasmid having sequences necessary to mobilize transfer of the SaADF2 construct from *E. coli* to *Agrobacterium*. Alternatively a simple freeze-thaw method, as used here, can be used to mobilize plasmid vectors into *Agrobacterium*. A recombinant *Agrobacterium* strain, containing the necessary sequences for plant transformation, is used to infect leaf discs or callus tissues derived from mature seeds, immature embryos, etc. Discs/callus tissues are grown on selection media and successfully transformed regenerants are identified.

Plant viruses also provide a possible means for transfer of exogenous DNA.

Direct uptake of DNA by plant cells can also be used. Typically, protoplasts of the target plant are placed in culture in the presence of the DNA to be transferred, along with an agent that promotes the uptake of DNA by protoplasts. Such agents include, for example, polyethylene glycol and calcium phosphate.

Alternatively, DNA uptake can be stimulated by electroporation. In this method, an electrical pulse is used to open temporary pores in a protoplast cell membrane, and DNA in the surrounding solution is then drawn into the cell through the pores. Similarly, microinjection can be used to deliver the DNA directly into a cell, preferably directly into the nucleus of the cell.

In many of these techniques, transformation occurs in a plant cell in culture. Subsequent to the transformation event, plant cells must be regenerated to whole plants. Techniques for the regeneration of mature plants from callus or protoplast culture are known for a large number of plant species. See, e.g., Handbook of Plant Cell Culture, Vols. 1-5, 1983-1989 McMillan, N.Y.

Alternate methods are also available that do not necessarily require the use of isolated cells and plant regeneration techniques to achieve transformation. These are generally referred to as "biolistic" or "particle acceleration" methods, in which DNA-coated metal particles are propelled into plant cells by either a gunpowder charge (see Klein et al., Nature 327: 70-73, 1987) or by electrical discharge (see EPO 270 356). In this manner, plant cells in culture or plant reproductive organs or cells, e.g. pollen, can be stably transformed with the DNA sequence of interest.

In certain dicots and monocots, direct uptake of DNA is a preferred method of transformation. For example, in maize or rice the cell wall of cultured cells is digested in a buffer with one or more cell wall-degrading enzymes, such as cellulase, hemicellulase, and pectinase, to isolate viable protoplasts. The protoplasts are washed several times to remove the degrading enzymes, and are then mixed with a plasmid vector containing the nucleotide sequence of interest. The cells can be transformed with either PEG (e.g. 20% PEG 4000) or by electroporation. The protoplasts are placed on a nitrocellulose filter and cultured on a medium with embedded maize cells functioning as feeder cultures. After 2-4 weeks, the cultures in the nitrocellulose filter are maintained in medium for 1-2 months. The nitrocellulose filters with the plant cells are transferred to fresh medium nurse cells every two weeks.

Other methods of transforming plants are described in B. Jenes et al., and in S. Ritchie et al., in S.-D. Kung et al. (Eds.), *Transgenic Plants*, vol. 1, Engineering and Utilization, Academic Press, Inc., Harcourt Brace Jovanovich (1993); and in L. Mannonen et al., *Critical Reviews in Biotechnology*, vol. 14, pp. 287-310 (1994). See also the various references cited on pages 15-17 of published international patent application WO 00/26390, each of which is incorporated by reference.

A vector that may be used to transform seeds, germ cells, whole plants, or somatic cells of monocots or dicots, is the transposon-based vector disclosed in U.S. Pat. No. 5,719,055. This vector may be delivered to plant cells through one of the techniques described above or, for example, via liposomes that fuse with the membranes of plant cell protoplasts.

The present invention can be applied to transform virtually any type of green plant, both monocot and dicot. Among the crop plants and other plants for which transformation is contemplated are (for example) rice, maize, wheat, millet, rye, oat, barley, *sorghum*, sunflower, sweet potato, cassava, alfalfa, sugar cane, sugar beet, canola and other *Brassica* species, sunflower, tomato, pepper, soybean, tobacco, melon, lettuce, celery, eggplant, carrot, squash, melon, cucumber and other cucurbits, beans, cabbage and other cruciferous vegetables, potato, tomato, peanut, pea, other vegetables, cotton, clover, cacao, grape, citrus, strawberries and other berries, fruit trees, and nut trees. The novel sequences may also be used to transform turf grass, ornamental species, such as *petunia* and rose, and woody species, such as pine and poplar.

Miscellaneous

Through routine breeding practices known in the art, progeny will be bred from successfully-transformed parent plants. Once progeny are identified that are demonstrably tolerant to abiotic stress, those progeny will be used to breed varieties and hybrids for commercial use. Crossing and back-crossing resistant plants with other germplasm through standard means will yield stress-tolerant varieties and hybrids having good productivity and other agronomically desirable properties. Alternatively, direct transformation into a variety or into a parent of a hybrid having agronomically desirable properties may be employed, as direct transformation can accelerate the overall selection and breeding process.

As used in the specification and claims, unless otherwise clearly indicated by context, the term "plant" is intended to encompass plants at any stage of maturity, as well as any cells, tissues, or organs taken or derived from any such plant, including without limitation any embryos, seeds, leaves, stems, flowers, fruits, roots, tubers, single cells, gametes, anther cultures, callus cultures, suspension cultures, other tissue cultures, or protoplasts. Also, unless otherwise clearly indicated by context, the term "plant" is intended to refer to a photosynthetic organism or green plant including algae, mosses, ferns, gymnosperms, and angiosperms. The term excludes, however, both prokaryotes, and eukaryotes that do not carry out photosynthesis such as yeast, other fungi, and the so-called red plants and brown plants that do not carry out photosynthesis.

Unless otherwise clearly indicated by context, the "genome" of a plant refers to the entire DNA sequence content of the plant, including nuclear chromosomes, mitochondrial chromosomes, chloroplast chromosomes, plasmids, and other extra-nuclear or extra-chromosomal DNA.

Unless otherwise clearly indicated by context, the "progeny" of a plant includes a plant of any subsequent generation whose ancestry can be traced to that plant.

Unless otherwise clearly indicated by context, a "derivative" of an SaADF2-transformed plant includes both the progeny of that plant, as the term "progeny" is defined above; and also any mutant, recombinant, or genetically-engineered derivative of that plant, whether of the same species or of a different species; where, in either case, the stress tolerance characteristics of the original plant have been transferred to the derivative plant. Thus a "derivative" of a plant could include, by way of example and not limitation, any of the following plants that express a stress-tolerant phenotype: $F_1$ progeny plants, $F_2$ progeny plants, $F_{30}$ progeny plants, a transgenic maize plant transformed with the SaADF2 gene, and a transgenic sweet potato plant so transformed.

The following definitions should be understood to apply throughout the specification and claims, unless otherwise clearly indicated by context.

An "isolated" nucleic acid sequence is an oligonucleotide sequence that is located outside a living cell. A cell comprising an "isolated" nucleic acid sequence is a cell that has been transformed with a nucleic acid sequence that at one time was located outside a living cell; or a cell that is the progeny of, or a derivative of, such a cell.

Other embodiments include: (a) A transformation vector comprising an SaADF2 polynucleotide. Or (b) A host cell comprising an SaADF2 polynucleotide. Or (c) A method for producing a plant having enhanced stress tolerance, comprising transforming plant cells with an SaADF2 polynucleotide, wherein the plants cells are capable of regenerating a plant. Or (d) A plant produced by such a method, wherein cells of the plant express the encoded SaADF2. Or (e) A derivative plant of such a plant, wherein cells of the derivative plant express the encoded SaADF2. Or (f) A seed of such a plant or derivative plant, or capable of producing such a derivative plant, wherein cells of the seed comprise an SaADF2 polynucleotide.

Other embodiments include: (a) A method for producing a plant having enhanced stress tolerance, the method comprising crossing or back-crossing such a plant or derivative plant with other germplasm to produce a progeny plant, wherein cells of the progeny plant express the encoded SaADF2. Or (b) A plant produced by such crossing or backcrossing, wherein cells of the plant express the encoded SaADF2. Or (c) A derivative of such a plant, wherein cells of the derivative plant express the encoded SaADF2. Or (d) A seed of such a plant or derivative plant, wherein cells of the seed comprise an SaADF2 polynucleotide.

Other embodiments include such a plant or derivative plant, wherein the plant is a monocot, or wherein the plant is a dicot.

The complete disclosures of all references cited in the specification are hereby incorporated by reference in their entirety, as is the complete disclosure of priority application Ser. No. 61/843,511. In the event of an otherwise irresolvable conflict, however, the disclosure of the present specification shall control.

What is claimed:

1. A plant cell comprising a polynucleotide encoding a polypeptide comprising SEQ ID NO:8 operably linked to a heterologous promoter.

2. The plant cell of claim 1, wherein the promoter comprises SEQ ID NO: 9.

3. The plant cell of claim 1, wherein the promoter is constitutive.

4. A plant or plant cell transformed with the p35S::SaADF2 vector, wherein said vector was deposited under ATCC Accession Number PTA-121363.

5. A method for producing a plant, said method comprising transforming one or more plant cells with a vector comprising a polynucleotide encoding a polypeptide comprising SEQ ID NO:8 operably linked to a stress inducible promoter, wherein the plant cells are capable of regenerating into a plant, wherein the plant cells are cells of a plant other than *Spartina* spp., and wherein, as compared to wild-type conspecific plants, the plant has enhanced tolerance to high salinity, drought, or low temperature stress.

6. A plant produced by the method of claim 5, wherein cells of said plant express the encoded polypeptide.

7. A derivative plant of the plant of claim 6, wherein cells of said derivative plant express the encoded polypeptide.

8. A seed of the plant of claim 6, or a seed capable of producing said plant, wherein cells of said seed comprise said polynucleotide.

9. A seed of the derivative plant of claim 7, or a seed capable of producing said derivative plant, wherein cells of said seed comprise said polynucleotide.

10. The plant of claim 6, wherein said plant is *Oryza sativa*.

11. The plant of claim 7, wherein said plant is *Oryza sativa*.

12. The plant of claim 6, wherein said plant is *Gossypium hirsutum*.

13. The plant of claim 7, wherein said plant is *Gossypium hirsutum*.

14. The plant of claim 6, wherein said plant is a monocot.

15. The plant of claim 6, wherein said plant is a dicot.

16. The plant of claim 7, wherein said plant is a monocot.

17. The plant of claim 7, wherein said plant is a dicot.

18. A method for producing a stress-tolerant plant, said method comprising crossing or back-crossing the plant of claim 6 with other germplasm to produce a progeny plant, wherein cells of said progeny plant express the encoded polypeptide.

19. A plant produced by the method of claim 18, wherein cells of said stress-tolerant plant express the encoded polypeptide, and wherein, as compared to wild-type conspecific plants, said plant has enhanced tolerance to high salinity, drought, or low temperature stress.

20. A method for producing a stress-tolerant plant, said method comprising crossing or back-crossing the plant of claim 7 with other germplasm to produce a progeny plant, wherein cells of said progeny plant express the encoded polypeptide.

21. A plant produced by the method of claim 20, wherein cells of said stress-tolerant plant express the encoded polypeptide, and wherein, as compared to wild-type conspecific plants, said plant has enhanced tolerance to high salinity, drought, or low temperature stress.

22. A seed of the plant of claim 19, or a seed capable of producing said plant, wherein cells of said seed comprise said polynucleotide.

23. A seed of the plant of claim 21, or a seed capable of producing said plant, wherein cells of said seed comprise said polynucleotide.

24. A method for growing plants, said method comprising planting a plurality of seeds of claim 8, and growing the resulting plants under one or more stresses selected from the group consisting of high salinity, drought, and low temperature stress conditions.

25. A method for growing plants, said method comprising planting a plurality of seeds of claim 9, and growing the resulting plants under one or more stresses selected from the group consisting of high salinity, drought, and low temperature stress conditions.

* * * * *

SEQUENCE LISTING

```
<160> NUMBER OF SEQ ID NOS: 9

<210> SEQ ID NO 1
<211> LENGTH: 26
<212> TYPE: DNA
<213> ORGANISM: Artificial sequence
<220> FEATURE:
<223> OTHER INFORMATION: Synthetic primer

<400> SEQUENCE: 1
ggaagatcta tggccttcat gcgcac                                          26

<210> SEQ ID NO 2
<211> LENGTH: 23
<212> TYPE: DNA
<213> ORGANISM: Artificial sequence
<220> FEATURE:
<223> OTHER INFORMATION: Synthetic primer

<400> SEQUENCE: 2
gggtaacctc agtgagcccg ctc                                             23

<210> SEQ ID NO 3
<211> LENGTH: 18
<212> TYPE: DNA
<213> ORGANISM: Artificial sequence
<220> FEATURE:
<223> OTHER INFORMATION: Synthetic primer

<400> SEQUENCE: 3
tacttctaca cagccatc                                                   18

<210> SEQ ID NO 4
<211> LENGTH: 18
```

```
<212> TYPE: DNA
<213> ORGANISM: Artificial sequence
<220> FEATURE:
<223> OTHER INFORMATION: Synthetic primer

<400> SEQUENCE: 4
tatgtcctgc gggtaaat                                                   18

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
atcgaggaaa agcaaaagca                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
cgatccttgg aggtggagta                                                 20

<210> SEQ ID NO 7
<211> LENGTH: 438
<212> TYPE: DNA
<213> ORGANISM: Spartina alterniflora
<220> FEATURE:
<221> NAME/KEY: misc_feature
<223> OTHER INFORMATION: Actin depolymerizing factor 2

<400> SEQUENCE: 7
atggccttca tgcgcaccca ctccaatgcc tcttctggta tgggagtcgc tcctaacatc      60
agggacacat tccacgagct tcagatgaag aaggctttcc gatatgttat cttcaaaatc     120
gaggaaaaac aaaagcaggt ggttgtggag aagactgggg ctactactga aagttatgat     180 gacttttttgg cctccctccc agagaatgac tgcagatatg ccctctatga ttttgatttt     240
gttactggag agaatgtgca gaaaagcaag atattttttca ttgcctggtc tccatctaca     300
tcccggattc gtgctaagat gctgtactcc acctccaagg atcgcatcaa gcatgaactt     360
gatgggtttc actacgagat ccaggcaaca gattcatcag aggtggacat tgatgtgctc     420
cgagagcggg ctcactga                                                  438

<210> SEQ ID NO 8
<211> LENGTH: 145
<212> TYPE: PRT
<213> ORGANISM: Spartina alterniflora
<220> FEATURE:
<221> NAME/KEY: misc_feature
<223> OTHER INFORMATION: Actin depolymerizing factor 2

<400> SEQUENCE: 8

Met Ala Phe Met Arg Thr His Ser Asn Ala Ser Ser Gly Met Gly Val
1               5                   10                  15

Ala Pro Asn Ile Arg Asp Thr Phe His Glu Leu Gln Met Lys Lys Ala
            20                  25                  30

Phe Arg Tyr Val Ile Phe Lys Ile Glu Glu Lys Gln Lys Gln Val Val
        35                  40                  45
```

```
Val Glu Lys Thr Gly Ala Thr Thr Glu Ser Tyr Asp Asp Phe Leu Ala
     50                  55                  60

Ser Leu Pro Glu Asn Asp Cys Arg Tyr Ala Leu Tyr Asp Phe Asp Phe
 65                  70                  75                  80

Val Thr Gly Glu Asn Val Gln Lys Ser Lys Ile Phe Phe Ile Ala Trp
                 85                  90                  95

Ser Pro Ser Thr Ser Arg Ile Arg Ala Lys Met Leu Tyr Ser Thr Ser
            100                 105                 110

Lys Asp Arg Ile Lys His Glu Leu Asp Gly Phe His Tyr Glu Ile Gln
            115                 120                 125

Ala Thr Asp Ser Ser Glu Val Asp Ile Asp Val Leu Arg Glu Arg Ala
            130                 135                 140

His
145

<210> SEQ ID NO 9
<211> LENGTH: 1875
<212> TYPE: DNA
<213> ORGANISM: Spartina alterniflora
<220> FEATURE:
<221> NAME/KEY: misc_feature
<223> OTHER INFORMATION: SaASr1 Promoter sequence including 5'UTR.  The
      A at position 1789 represents the transcription start site.

<400> SEQUENCE: 9
ggtgcgtgaa gatggaggta ccttgtggtt gcgctagatg ctgcgagtag ccggtttaga    60
ttttgtagtg caggcttttt gggttcgtgc cagttgccaa tttgtggtct cgtgttttca   120
tgctttgctc agtttcttct tctttgcttt ttctttgtgc ttgagctagg tgctccctag   180
cttgtttatc tgtaattgct atctttttaa tgaaatacgc gctcatatgt gtgttcgcta   240
aaaaaagttt ttcggggaac ctgagttctc acaagtagag gaaaggggga gacaaataaa   300
gttggaacat tggccaacat ctcgttttca agaagctatt aagaatcatg gtgcttcttt   360
ttgcacccat aggatcaaca cagatttttt gtttgtgtgt ggttacaata gatggatgta   420
gcccaatttg tcaaattagc ttttgctggt tgcacttgaa tattctaaat tagcatcata   480
taagaatatc tgtcatatat tccttgtcac acttactgct gagtgttagt gcgtttcagt   540
ttcaggaggg aaataattaa taaaaaataa cacataatga tactcgaggc tcttatatag   600
ctatagtcaa atagaataat tccacatgtc agttatccta ataagcgtgc cattccaaaa   660
taataataat aatgaattct acatacatgg aaggtaacac tatctcttgg aatttattct   720
tgctgacatg aatgaacaga gttggttaag tgtctcgatt cattgataag acttaaaagt   780
ctattcaaaa tcaggatgca aataaagagg aataaatatc ttggtttaga gtcgccgtat   840
cgttcgatat cttttccagg cagccgacac cttctccctc tcgtgtgtcc caattgcacc   900
gtgtcaccat ctttccttttt ccaattgcat cgcatcatga tcttaccttt atccaaagtt   960
aatatcgatg gaggaaaaga ttgcaagagg ttgcttaagc cacaaacaac atcatcacaa  1020
gcatgcatat gtattgctgt ggatcacatt taagtcactg agattaatat ttctttgtgg  1080
aaagttttgc caattggccc gttgatttgc tctgaaaagt ttgcagacgc tgataggaaa  1140
aaatcgtgta ctctaggcct tccacaattc tgaaccttga ggtacacaga gaatacagaa  1200
attaatttga aggatacaaa aatttagcac ttttcaagat gaccacttca aaacatctga  1260
gcttcatgca gttatctttt ttttacggaa catgcagtca tctttctttt ttgacgcgaa  1320
agcagtcatc tttctaatac taatatccga atattccaag gattatcctc tgccgacagt  1380
```

```
ttagctcatc tgctcatgct tccatttctt cgattagagg ataaccaatg gttagctcaa    1440
gtggctggtc agtgggtcct gccgtccaat aactgtccgg gccccacgcc acttgatgcc    1500
gtcatgggca ggcatccgtg gtgccaactg ccgagttatt agcaacttat ttccgattta    1560
gtccctgctc cactatccat caattttgaa acaattgaat tcctttggga aaaaatccat    1620
ctaatcgttt gattaatctg cacagcatag atgagcaatt ttattatgta ctgtatcctt    1680
tgctagctac tccacatcac agtgtgttaa tcacaatcac cctttgcagt ttgcaccgtc    1740
catcgatctc tccgcctata taacaacacg gcgtcgtgcc gaggctccaa cccacaacca    1800
gtcaactaag ctagccatcg tccaactgtc actgctgtca gctctcaatc gcacaccgat    1860
cggtcccggc cggcc                                                    1875
```